US005957951A

United States Patent [19]

Cazaux et al.

[11] Patent Number: 5,957,951

[45] Date of Patent: Sep. 28, 1999

[54] PORTABLE DEVICE FOR ACUPUNCTURE-TYPE PERCUTANEOUS TREATMENT

[76] Inventors: Patrick Cazaux, 1 rue de Bearn, 92 210 Saint-Cloud, France; Michel Doppelt, 1 bis rue Castela, 92 100 Boulogne Billancourt, France

[21] Appl. No.: 09/098,557

[22] Filed: Jun. 17, 1998

[30] Foreign Application Priority Data

Mar. 6, 1998 [FR] France .................................. 98 02873

[51] Int. Cl.[6] .................................................. A61B 17/00

[52] U.S. Cl. .......................................... 606/204; 607/148

[58] Field of Search .................................. 606/189, 191, 606/204, 185; 607/59, 65, 72, 148

[56] References Cited

U.S. PATENT DOCUMENTS 3,957,053 5/1976 Woo ....................................... 606/189
5,010,896 4/1991 Westbrook ............................. 607/148
5,735,868 4/1998 Lee ......................................... 606/189
5,861,017 1/1999 Smith et al. ............................ 607/59

*Primary Examiner*—Michael Buiz
*Assistant Examiner*—Kevin Truong
*Attorney, Agent, or Firm*—Armstrong, Westerman, Hattori, McLeland & Naughton

[57] ABSTRACT

A portable, self-powered device for acupuncture-type percutaneous treatment comprising a casing having on its bottom a plurality of metallic contact blocks, each contact block constituting the terminal of a pulse generator mounted in this casing, means provided for removably attaching the casing on a portion of a patient's body, and an electronic program comprising seven therapeutic functions for connecting at least two contact blocks to the pulse generator, the connections with the contact blocks being chosen in accordance with the condition to be treated. An application for the device is in particular the treatment of obesity.

20 Claims, 3 Drawing Sheets

PORTABLE DEVICE FOR ACUPUNCTURE-TYPE PERCUTANEOUS TREATMENT

BACKGROUND OF THE INVENTION

The present invention concerns a portable, self-powered device for acupuncture-type percutaneous treatment, of the type comprising a casing having on its bottom at least one contact block constituting the terminal of an impulse generator mounted in said casing, and means provided for attaching the casing on a portion of a patient's body.

Devices for percutaneous treatment of a patient using electric stimulation are known. For example, patent document FR-A-2 513 514 describes a device comprising a module having a surface intended to be applied against a portion of a patient's body and conductors whose end parts are immobilized in the module and protrude from the surface, which is applied against the body, in areas corresponding to acupuncture points of the patient's body specific to a predetermined therapy. The protruding parts have a diameter in the order of a millimeter and a distance to the edges of the surface of 0.5 to 1 mm. The conductors are intended to transmit electric pulses and a generator provides pulses at a voltage of 1 to 9 volts.

Patent document GB-A-2 148 717 describes a portable belt comprising an electrical circuit including a transformer, a battery, and at least one electrode having the form of a buffer whose concave surface enables the electrode to adapt easily to the particular area where a treatment is intended to be applied. An electrode can be mobile along a path.

Patent document GB-A-2 216 800 describes a device for massaging the eyes which enables the relaxation of the muscles around the eyes and the stimulation of blood circulation in these muscles. Such a device comprises a flexible belt having a plurality of protruding massaging elements which are symmetrically distributed. The elements are electrically connected together as well as to a low frequency generation source which produces continuous, low frequency pulses. The elements have different oval shapes with flat or convex surfaces, and they are positioned in different areas of the belt so as to act on different massaging points.

Patent document FR-A-2 662 076 describes a portable, self-powered device for acupuncture-type percutaneous treatment comprising a casing having on its bottom at least one metallic contact block, the contact block constituting the output terminal of a pulse generator mounted in the casing, and means provided for removably attaching the casing on a portion of a patient's body. The pulse generator comprises means for presetting the amplitude (from 1 to 12 volts), the duration (100 milliseconds to 2 seconds) and the frequency (0.5 to 10 Hertz) of the pulses. A diode is connected to the output of the pulse generator parallel to the contact blocks so as to blink at the frequency produced by the generator, said diode being mounted on the casing, preferably on its top part.

All the devices described above only enable the treatment of one condition of a patient. However, it is desirable to treat several conditions with the same device. For example, it is desired to treat obesity and stresses such as anxiety, phobia, spasmophilia, and stage fright; to improve memory, and to alleviate tobacco addiction, impotence, frigidity, nausea, vomiting, and motion sickness, all with the same device.

SUMMARY OF THE INVENTION

To achieve this design, the invention provides a portable, self-powered device for acupuncture-type percutaneous treatment comprising a casing having on its bottom a plurality of metallic contact blocks, each contact block constituting the output terminal of a pulse generator mounted in said casing, means provided for removably attaching the casing on a portion of a patient's body, and an electronic program comprising seven therapeutic functions for connecting the contact blocks with the pulse generator, the connections with the contact blocks being chosen according to the particular condition to be treated.

More precisely, the contact blocks are arranged according to a grid or an array of three rows by three columns, the first row having contact blocks referenced C6, C5, C7, the second row being constituted by a ground, contact block CS6 and contact block CS7, and the third row being constituted by contact blocks P7, P9. Preferably, contact blocks P7 and P9 are oriented toward the user's thumb and contact blocks C6, C5, C7 are oriented toward the auricular finger when the device is positioned on the patient's wrist.

The contact blocks may be simultaneously connected to the pulse generator to receive pulses in the following manner to treat the indicated condition:

to fight obesity: C7, C5, P9, P7 to fight stress (anxiety, phobia, spasmophilia, stage fright): C7, C5, CS7, P9 to fight insomnia: C6, C5, C7, CS6, P9 to improve memory: CS6, P9, C7 to fight tobacco addiction: C6, C7, P9 to fight impotence, frigidity: C7, CS6 to fight nausea, vomiting, motion sickness: CS6, C9

According to the invention, it is advantageous if a switch is provided which comprises a blinking diode, and if pulses of one second of duration are sent every three seconds, and forty cycles of this three-second period are carried out during the operation of the device which lasts for example two minutes.

The device may comprise a battery, or a solar panel, or both, for a power supply.

Some contact blocks may be of different metals or metal alloys than the others. Further, the contact blocks may be magnetized. Still further, they may be slightly pointed so as to better stimulate acupuncture points.

DESCRIPTION OF AN EMBODIMENT

The following description of a particular embodiment of the present invention with reference to the annexed drawings does not limit the scope of the invention but will allow a better understanding of how the invention may be practiced.

Figure 1:
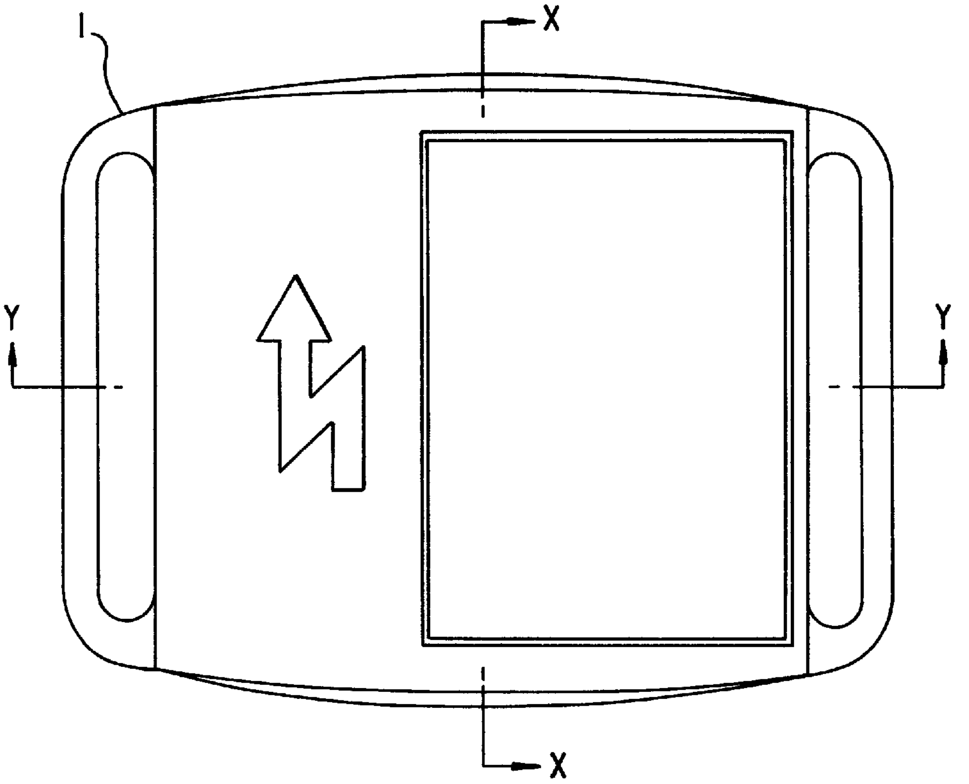
FIG. 1 is a plan view of a device according to the present invention without armband.
Figure 2:
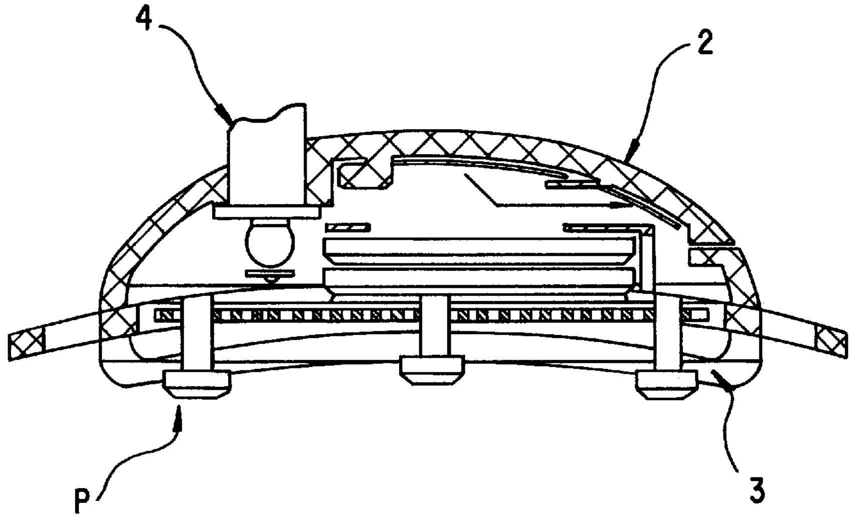
FIG. 2 is a sectional view along line YY of the device of FIG. 1.

FIGS. 1 and 2 represent a device according to the invention, which comprises a metallic frame 1, a rounded casing 2 and a base 3. The metallic frame 1 as well as the base 3 are slightly curved so as to adapt to a patient's wrist. Contact blocks P protrude from the base 3 and may be applied against a patient's wrist. A switch button 4 protrudes from the casing 2. Said switch button 4 is provided with a blinking diode 4*a* which blinks during the whole duration of the treatment period, such as, for example, two minutes.

Figure 3:
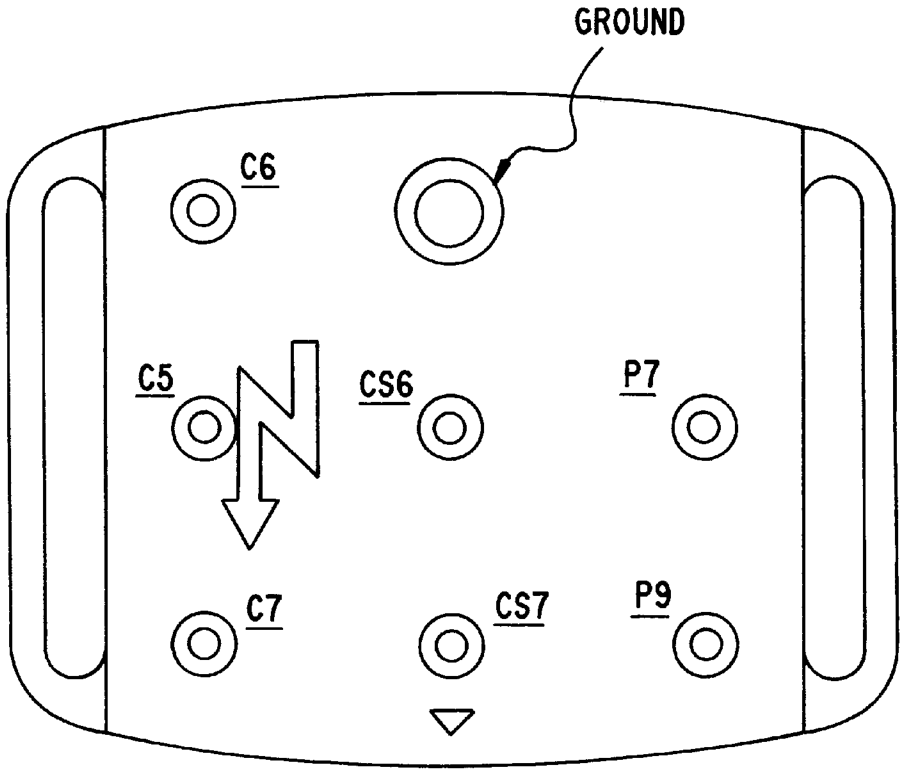
FIG. 3 is a bottom view of the device of FIG. 1.
Figure 4:
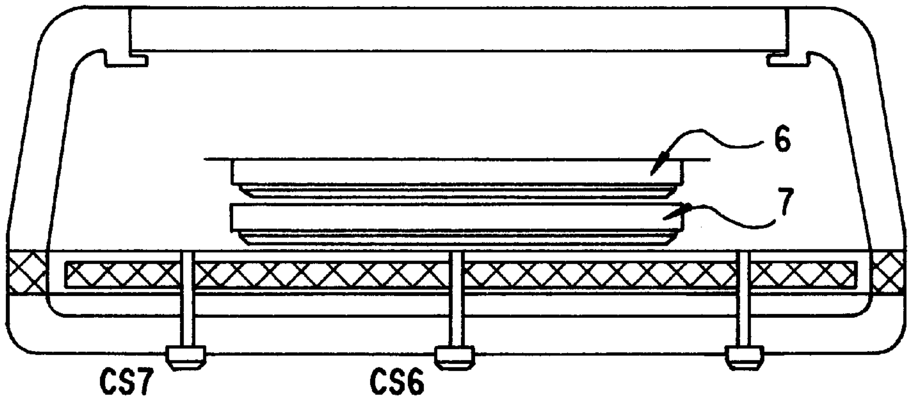
FIG. 4 is a sectional view along line XX of the device of FIG. 1.

As can be seen on FIG. 3, the contact blocks are arranged in a grid or array of three rows and three columns, the first row comprising contact blocks C6, C5, C7, the second row comprising a ground and contact blocks CS6 and CS7, and the third row comprising only two contact blocks P7 and P9. Contact blocks P7, P9 are situated on the side facing the patient's thumb. The contact blocks constitute an output band of a pulse generator mounted in the casing.

Figure 5:
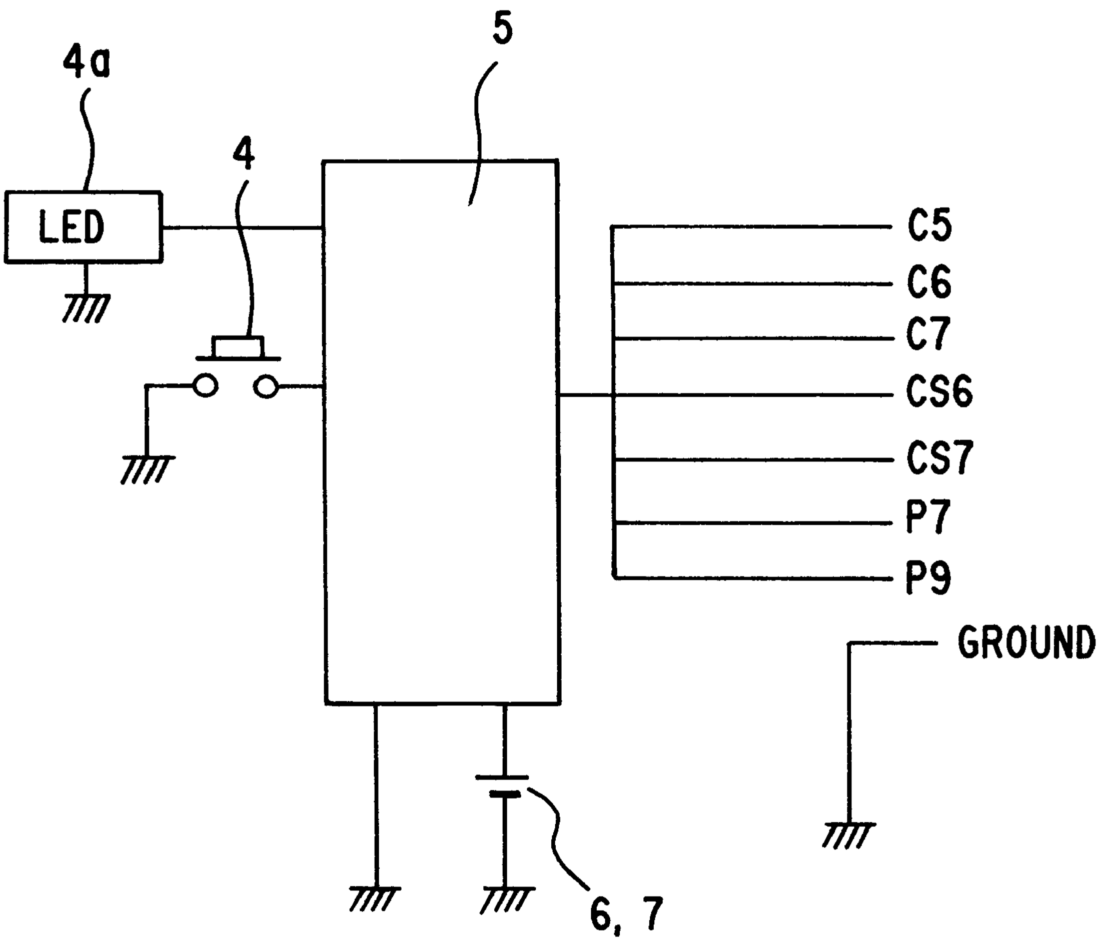
FIG. 5 is a schematic view of connections between contact blocks and a microprocessor.

FIG. 5 is a schematic showing the connections between contact blocks C5, C6, C7, CS6, CS7, P7, P9, and the ground with the microprocessor 5 which is powered up by two batteries 6 and 7 by means of switch button 4.

The contact blocks are connected together during assembly of the device according to the present invention, power is supplied to the device by means of the two three-volt batteries 6 and 7 and the pulses at the contact blocks are at a voltage of 5 to 6 Volts. The pulses may last for one second and are provided every three seconds in a cycle, and are repeated for 40 cycles.

The contact blocks may be simultaneously connected to the pulse generator to receive pulses in the following manner so as to treat the indicated condition:

to fight obesity: C7, C5, P9, P7 to fight stress (anxiety, phobia, spasmophilia, stage fright): C7, C5, CS7, P9 to fight insomnia: C6, C5, C7, CS6, P9 to improve memory: CS6, P9, C7 to fight tobacco addiction: C6, C7, P9 to fight impotence, frigidity: C7, CS6 to fight nausea, vomiting, motion sickness: CS6, C9

As shown in FIG. 5, the light-emitting diode 4*a* is mounted at the output of the pulse generator parallel to the contact blocks and blinks at the frequency provided by the generator.

According to another embodiment of the invention, the device may utilize a power source constituted by a solar panel.

According to another embodiment of the invention, some of the contact blocks may be constituted of different metals or different alloys which are more or less conducting so as to allow a better stimulation of the acupuncture points.

Preferably, the contact blocks are in the shape of truncated cones, the smaller base of the cone being applied against the patient's skin on the underside of the wrist. However, all the contact blocks may be pointed, or only some of them may be pointed. The casing may be made from thermosetting plastic.

What is claimed is:

1. A portable, self-powered device for acupuncture-type percutaneous treatment comprising a casing having on its bottom a plurality of metallic contact blocks, each of said contact blocks constituting the terminal of a pulse generator mounted in said casing, means provided for removably attaching the casing on a portion of a patient's body, and an electronic program comprising seven therapeutic functions for connecting at least two contact blocks to the pulse generator, the connections with the contact blocks being chosen in accordance with the condition to be treated in said patient.

2. A device according to claim 1, wherein the contact blocks are arranged in an array comprising three rows and three columns, the first row comprising three contact blocks C6, C5, C7, the second row being constituted by a ground, contact block CS6 and contact block CS7, and the third row being constituted by contact blocks P7, P9, contact blocks P7, P9 being oriented toward the patient's thumb and contact blocks C6, C5, C7 being oriented toward the auricular finger when the device is positioned on the patient's wrist.

3. A device according to claim 2, further including a switch comprising a diode which blinks, and wherein pulses having a duration of one second are sent every three seconds and forty cycles of this three-second period are carried out during the operation of the device which lasts two minutes.

4. A device according to claim 2, comprising a battery for power supply for the pulse generator.

5. A device according to claim 2, comprising a solar panel for power supply for the pulse generator.

6. A device according to claim 2, wherein some contact blocks are in different metals than the others.

7. A device according to claim 2, wherein the contact blocks are magnetized.

8. A device according to claim 2, wherein the contact blocks are slightly pointed.

9. A device according to claim 1, wherein the contact blocks are arranged in an array comprising three rows and three columns, the first row comprising three contact blocks C6, C5, C7, the second row being constituted by the ground, contact block CS6 and contact block CS7, and the third row being constituted by contact blocks P7, P9, contact blocks P7, P9 being oriented toward the patient's thumb and contact blocks C6, C5, C7 being oriented toward the auricular finger when the device is positioned on the patient's wrist, and the contact blocks being simultaneously connected to the pulse generator to receive pulses in the following manner to treat the indicated condition:

to fight obesity: C7, C5, P9, P7 to fight stress (anxiety, phobia, spasmophilia, stage fright): C7, C5, CS7, P9 to fight insomnia: C6, C5, C7, CS6, P9 to improve memory: CS6, P9, C7 to fight tobacco addiction: C6, C7, P9 to fight impotence, frigidity: C7, CS6 to fight nausea, vomiting, motion sickness: CS6, C9.

10. A device according to claim 9, further including a switch comprising a diode which blinks, and wherein pulses having a duration of one second are sent every three seconds and forty cycles of this three-second period are carried out during the operation of the device which lasts two minutes.

11. A device according to claim 9, comprising a battery for power supply for the pulse generator.

12. A device according to claim 9, comprising a solar panel for power supply for the pulse generator.

13. A device according to claim 9, wherein some contact blocks are in different metals than the others.

14. A device according to claim 9, wherein the contact blocks are magnetized.

15. A device according to claim 1, further including a switch comprising a diode which blinks, and wherein pulses having a duration of one second are sent every three seconds, and forty cycles of this three-second period are carried out during the operation of the device which lasts two minutes.

16. A device according to claim 1, comprising a battery for power supply for the pulse generator.

17. A device according to claim 1, comprising a solar panel for power supply for the pulse generator.

18. A device according to claim 1, wherein some contact blocks are in different metals than the others.

19. A device according to claim 1, wherein the contact blocks are magnetized.

20. A device according to claim 1, wherein the contact blocks are slightly pointed.

* * * * *